US006479565B1

(12) United States Patent
Stanley

(10) Patent No.: US 6,479,565 B1
(45) Date of Patent: Nov. 12, 2002

(54) BIOACTIVE CERAMIC CEMENT

(76) Inventor: Harold R. Stanley, 2 Sea Oats Ter., Ormond Beach, FL (US) 32176-2133

( * ) Notice: Subject to any disclaimer, the term of this patent is extended or adjusted under 35 U.S.C. 154(b) by 0 days.

(21) Appl. No.: 09/374,778

(22) Filed: Aug. 16, 1999

(51) Int. Cl.$^7$ ................................. A61F 2/16; A61F 2/28
(52) U.S. Cl. ....................... 523/114; 523/115; 523/116; 523/122; 424/426; 623/16; 623/923
(58) Field of Search ................................. 523/115, 116, 523/122, 114; 264/1.7; 501/12, 39, 57, 58; 623/16.11, 923

(56) References Cited

U.S. PATENT DOCUMENTS

| | | | |
|---|---|---|---|
| 3,971,754 A | | 7/1976 | Jurecic |
| 4,224,023 A | | 9/1980 | Cheung |
| 4,718,910 A | * | 1/1988 | Draenert ...................... 523/116 |
| 4,725,234 A | | 2/1988 | Ethridge ...................... 433/215 |
| 4,758,612 A | | 7/1988 | Wilson et al. .................. 524/5 |
| 4,772,203 A | | 9/1988 | Scheunemann .............. 433/173 |
| 4,775,646 A | * | 10/1988 | Hench et al. ................... 501/2 |
| RE33,100 E | | 10/1989 | Ibsen et al. .................... 106/35 |
| 4,904,264 A | | 2/1990 | Scheunemann .............. 623/16 |
| 5,079,277 A | | 1/1992 | Wilson et al. ............... 523/116 |
| 5,218,035 A | | 6/1993 | Liu ............................. 524/414 |
| 5,453,456 A | | 9/1995 | Mitra et al. .................. 523/116 |
| 5,874,101 A | * | 2/1999 | Zhong et al. ............... 424/426 |
| 5,914,356 A | * | 6/1999 | Erbe ........................... 523/114 |
| 6,010,713 A | * | 1/2000 | Zhong et al. ............... 424/426 |
| 6,171,986 B1 | * | 1/2001 | Zhong et al. ................. 501/12 |

FOREIGN PATENT DOCUMENTS

| | | | |
|---|---|---|---|
| GB | 2094326 | * | 9/1982 |
| WO | WO 91/17777 | | 11/1991 |

OTHER PUBLICATIONS

Andersson, O. H., and Kangasniemi, L. (1991). Calcium phosphate formation at the surface of bioactive glass in vitro. J. Biomed. Mater. Res., 25, 1019–1030.

Andersson, O. H., Rosenqvist, J., and Karlsson, K. H. (1993). Dissolution, leaching, and $Al_2O_3$ enrichment at the surface of bioactive glasses studied by solution analysis. J. Biomed. Mater. Res., 27, 941–948.

Chang, R. W. (1996). A Cost–effectiveness Analysis of Total Hip Arthroplasty for Osteoarthritis of the Hip. JAMA. vol. 275, No. 11.

Clark, A. E., Pameijer, C. H., and Stanley, H. R. (1996). "Bioglass ® as a pulpcapping agent". J. Dent. Res. 75 Special Issue. Abstract #2104, p. 280.

Filgueriras, R. M., La Torre, G., and Hench, L. L. (1993). Solution effects on the surface reactions of a bioactive glass. J. Biomed. Mater. Res., 27, 445–453.

Filgueriras, R. M. (1993) Solution Effects on the Surface Reaction of Three Bioactive Glass Compositions. J. Biomed. Mater. Res., vol. 27, 1485–1493.

Frigstad, J. R., Kang, Y. H., and Park, J. B. (1997). "Reinforcement of PMMA bone cement with a continuous wire coil: a canine implantation study". Transactions of Society for Biomaterials, New Orleans, La., Apr. 30–May 4, p. 239.

Fritsch, E. W. (1996). "Static and fatigue properties of two new low–viscosity PMMA bone cements improved by vacuum mixing". J. Biomed. Mater. Res. 31: 451–456.

Gainey, G. M., Landesberg, R. L., and Katz, R. W. "Binding of osteoblast cell lines to extra cellular matrix proteins". J. Dent Res. (1998) 77 Special Issue A, Abstract #861, p. 213.

Gross, K. A., Berndt, C. C, Goldschlag, D. D., and Iacono, V. J. (1997). "In vitro changes of hydroxyapatite coatings". Int. J. Oral Maxillofac. Implants 12: 589–597.

Hench, L. L. (1991). Bioceramics: From concept to clinic. J. Am. Ceram. Soc. 74, 1487–1510.

Hench, L.L. (1997). Bioceramics: Centennial Feature. J. Am. Ceram. Soc., vol. 81 No. 7, pp. 1705–1727.

Hench, L. L. (1998). "Bioactive materials, The potential for tissue regeneration". J. Biomed. Mater. Res. 41: 511–518.

Hench, L. L., and Ethridge, E. C. (1982). Biomaterials: An Interfacial Approach. Academic Press, New York, Chaps. 5, 7, 14.

James, R. (1984). Tissue response to dental implant devices. In Clinical Dentistry, vol. 5 (J. W. Clark, ed.). Harper & Row, Philadelphia, Chap. 48, pp. 8–9.

Jonck, L. M., Grobbelaar, C. J. and Strating, H. (1989). "The biocompatibility of a glass–ionomer cement in joint replacement: bulk testing". Clinical Mater. 4: 85–107.

Jonck, L. M., Grobbelaar, C. J. and Strating, H. (1989). "Biological evaluation of glass–ionomer cement (Ketac–O) as an interface material in total joint replacement. A screening test". Clin. Mater. 4: 201–224.

Kangasniemi, I. M. O., Vedel, E., de Blick–Hogerworst, J., Yli–Urpo, A. U., and de Groot, K. (1993). Dissolution and scanning electron microscopic studies of Ca, P particle–containing bioactive glasses. J. Biomed. Mater. Res., 27, 1225–1233.

Kim, C. Y., Kim, J., and Chang, S. Y. (1993). Hydroxyapatite formation on bioactive glass in a solution with different pH and P–ion concentration. Trans. 19th Annual Meeting Soc. Biomaterials, Apr. 28–May 2, Birmingham, Alabama, p. 4.

(List continued on next page.)

Primary Examiner—Margaret Medley
(74) Attorney, Agent, or Firm—Van Dyke & Associates, P.A.; Timothy H. Van Dyke; Joseph Fischer

(57) ABSTRACT

The present invention provides a solution to the problems with known cements by providing a composition comprising (a) microscopic anhydrous pellets or particles containing the most important components of biological fluids or synthetic biological fluids (SBFs), (b) bioactive glass or other bioactive ceramic particles and (c) an appropriate resin such as, but not limited to, bisphenol-alpha-glycidyl methacrylate (BIS-GMA), to form a bone-forming cement which enhances (accelerates) bone production and bone bonding.

31 Claims, No Drawings

OTHER PUBLICATIONS

Kokubo, T., Kushitani, H., Sakka, S., Kitsugi, T. and Yamamuro, T. (1990). "Solutions–able to reproduce in vivo surface–structure changes in bioactive glass–ceramic A–W." J. Biomedical Materials Research, 24: 721–734. (Quoted by Filgueriras et al 1993).

Kokubo, T., Yoshihara, N., Nishimura, T., Yamamuro, T., and Nakamura, T., 1991, Bioactive bone cement based on $CaO-SiO_2-P_2O_5$ glass. J. Am. Ceram. Soc 74: 1739.

Lee, R. R., Ogiso, M., Watanabe, A., and Ishihara, K. (1997). "Examination of hydroxyapatite filled 4–META/MMA–TBB adhesive bone cement in vitro and in vivo environment". J. Biomed. Mater. Res. (Appl Biomater.) 38: 11–16.

Li, P., Bakker, D., and Van Blitterswijk, C. A. (1997). "The bone–bonding polymer Polyactive® 80/20 induces hydroxycarbonate apatite formation in vitro". J. Biomed. Mater. Res. 34: 79–86.

Li, P., Ohtsuki, C., Kokubo, T., Nakanishi, K., Soga, N., Nakamura, T., and Yamamuro T. (1993). Effects of ions in aqueous media on hydroxyapatite induction by silica gel and its relevance to bioactivity of bioactive glass and glass–ceramics. J. Appl. Biomat., 4, 221–229.

Li, P., Qui, Q., and Ducheyne, P. (1997). "Surface transformation of titanium to apatite affecting mineralization of extra cellular matrix in rat marrow stromal cell culture". Transactions of Society for Biomaterials, New Orleans, La., Apr. 30–May 4, p. 384.

Lu, H–Y., Helen, Pollack, S. R., and Ducheyne, P. "Relationship between surface charge and the formation of a calcium phosphate layer on bioactive glass in vitro". Transactions of Society for Biomaterials, New Orleans, La., Apr. 30–May 4, 1997, p. 126.

Lu, X., Topoleski, L. D. T., and Neerchal, N. K. "The influence of notch tip geometry on fatigue crack initiation in PMMA bone cement". Transactions of Society for Biomaterials, New Orleans, La., Apr. 30–May 4, 1997, p. 235.

Moreau, M. F., Chappard, D., Lesourd, M., Montheard, J. P., and Basle, M. F. (1998). "Free radicals and side products released during methylmethacrylate polymerization are cytotoxic for osteoblastic cells". J. Biomed. Mater. Res. 40: 124–131.

Morita, S., Yamamoto, H., Furuya, K., Ishihara, K., and Nakabayashi, N. (1997). "Enhanced strength in cemented stem fixation using adhesive acrylic cement as a metal coating material." J. Biomed. Mater. Res. 34: 171–175.

Nicholson, J. W., Brookman, P. J., Lacy, O. M., and Wilson, A. D., (1988). Fourier transform infrared spectroscopic study of the role of tartaric acid in glass–ionomer dental cements. J. Dent. Res. 67: 1451–1454.

Ogino, M., and Hench, L. L. (1980). Formation of calcium phosphate films on silicate glasses. J. Non–Cryst. Solids, 38–39, 673–378.

Ogino, N., Ohuchi, F., and Hench, L. L. (1980). Compositional dependence of the formation of calcium phosphate fibers on Bioglass®. J. Biomed. Mater. Res., 14, 55–64 (quoted by Hench, 1991).

Otsuka, M., Matsuda, Y., Yu, D., Wong, J., Fox, J.L., and Higuchi, W.I. (1990). A novel skeletal drug delivery system for anti–bacterial drugs using self–setting hydroxyapatite cement. Chem. Pharm. Bull 38:3500–3502.

Otsuka, M., Mastsuda, Y., Kokubo, T., Yoshihara, S., Nakamura, T., and Yamamuro, T. (1992). New skeletal drug delivery system containing antibiotics using self–setting bioactive glass cement. Chem. Pharm. Bull 40:3346–3348.

Otsuka, M., Mastsuda, Y., Kokubo, T., Yoshihara, S., Nakamura, T., and Yamamuro, T. (1995). Drug release from a novel self–setting bioactive glass bone cement containing cephalexin and its physiochemical properties. J. Biomed. Mater. Res. 29:33–38.

Planell, J. A., Vila, M. M., Gil, F. J., and Driesseny, F. C. M. (1995). "Acrylic bone cements". In Encyclopedic Handbook of Biomaterials and Bioengineering, Part B: Applications, vol. 2, Chapter 32, pp. 879–921. Edit by D. L. Wise et al, Marcel Dekker, Inc., New York.

Radin, S., Ducheyne, P., and Falaize, S. (1997–A). "Sol–gel–derived glass (SG) with a controlled surface reactivity". Transactions of Society for Biomaterials, New Orleans, La., Apr. 30–May 4, 1997, p. 161.

Radin, S., Ducheyne, P., Reicin, K. E., and Lee, M. H. (1997–B). "The effect of composition and in vitro immersion on the formation of a bioactive surface on sol–gel derived glass". Transactions of Society for Biomaterial, New Orleans, La. Apr. 30–May 4, p. 340.

Salvati, E.A., Callaghen, J.J., Brause, B.D., Klein, R.F., and Small, R.D. (1986). Reimplantation in infection: elution of gentamicin from cement and beads. Clin. Orthop., 207, 83. (Quoted by Otsuka et al 1995).

Stanley, H. R. (1996). A New Type of Bioactive Glass Bone: Cement for Joint Fixation. Division of Oral Diagnostic Science, College of Dentistry, University of Florida, Gainesville, FL.

Stanley, H. R., (1987). Implantology and the development of Bioglass. In The 1987 Dental Annual (D.D. Derrick, ed.). John Wright & Sons, Bristol, pp. 209–230.

Stanley, H. R. (1995). "Alveolar ridge maintenance using endosseously placed Bioglass® (45S5) cones". Encyclopedic Handbook of Biomaterials and Bioengineering, Part B: Applications vol. 2: 1559–1616, Ed. by D. L. Wise et al. Marcel Dekker, Inc. New York.

Stanley, H. R., Hall, M. B., Clark, A. E., King, C. J. III., Hench, L. L., and Berte, J. J. (1997). "Using 45S5 Bioglass cones as endosseous ridge maintenance implants to prevent alveolar ridge resorption: A 5–year evaluation." Int. J. Maxillofac Implants 12: 95–105.

Stanley, H. R., Hall, M. B., Colaizzi, F., and Clark, A. E. (1987). Residual alveolar ridge maintenance with a new endosseous implant material. J. Pros. Dent., 58, 607–613.

Stanley, H. R., Hench, L. L., Bennett, C. G., Jr., Chellemi, S. J., King, C. J., III, Going, R. E., Ingersoll, N. J., Ethridge, E. C., Kreutziger, K. L., Loeb, L., and Clark, A. E. (1981). The implantation of natural tooth form Bioglass in baboons—Long term results. Int. J. Oral Implant, 2, 26–38.

Stanley, H. R., Hench, L. L., Going R., Bennett, C., Chellemi, S. J., King, C. J., III, Ingersoll, N., Ethridge, E., and Kreutziger, K. (1976). The implantation of natural tooth form Bioglasses in baboons: A preliminary report. Oral Surg Oral Med Oral Pathol 1976; 42: 339–356.

Steflik, D. E., Corpe, R. S., Lake, F. T., Young, T. R., Sisk, A. L., Parr, G. R., Hanes, P. J., and Berkery, D.J. "Ultrastructural analyses of the attachment (bonding) zone between bone and implanted biomaterials". J. Biomed. Mater. Res. 39: 611–620.

Tamura, J., Kawanabe, K., Yamamuro, T., Nakamura, T., Kokubo, T., Yoshihara, S., and Shibuya, T. (1995). "Bioactive bone cement: the effect of amounts of glass powder and histologic changes with time". J. Biomed. Mater. Res. 29: 551–559.

Vazquez, B., Elvira, C., Levenfeld, B., Pascual, B., Goni, I., Gurruchaga, M., Ginebra, M. P., Gil, F. X., Planell, J. A., Liso, P. A., Rebuelta, M., and San Roman, J. (1997). "Application of tertiary amines with reduced toxicity to the curing process of acrylic bone cements." J. Biomed. Mater. Res. 34: 129–136.

Vrouwenvelder, W. C. A., Groot, C. G., and de Groot, K. (1993). Histological and biochemical evaluation of osteoblasts cultured on bioactive glass, hydroxylapatite, titanium alloy, and stainless steel. J. Biomed. Mater. Res., 27, 465–475.

Walsh, H. A., McCabe, J. P., Parks, M. L., Wright, T. M., Salvati, E. A., and Li, S. "Effect of altered polymarization rate on the mechanical properties of two brands of bone cement". Transactions of Society for Biomaterials, New Orleans, La., Apr. 20–May 4, 1997, p. 398.

West, J. K., and Hench, L. L. (1993). Molecular orbital modeling of bioactive glass reactions of stages 3 and 4. Trans. 19th Annual Meeting Soc. Biomaterials, Birmingham, Alabama, p. 2 (abstract).

Willert, H. G., Ludwig, J., and Semlitsch, M. (1974). "Reaction of bone to methacrylate after hip arthroplasty". The Journal of Bone & Joint Surgery 56–A, No. 7, Oct. 1974, pp. 1368–1382.

Wilson, A. D., (1977). The development of glass–ionomer cement? Dent. Update (Oct.): 401–412.

Wilson, A. D., and Kent, B. E. (1971). The glass–ionomer cement, a new translucent dental filling material, Jrl. of Applied Chemistry and Biotechnology vol. 21 p. 318.

Wilson, A. D. and McLean, J. W. (1988). "Glass–ionomer cement". Quintessence Publishing Co., Inc. Chicago.

Wilson, A. D., and Prosser, H. J., (1982). Biocompatibility of the glass–ionomer cement. J. Dent. Assoc. S. Afr. 37: 872–879.

Wilson, A. D., Prosser, H. J., and Powis, D. R. (1983). Mechanism of adhesion of polyelectrolyte cements to hydroxyapatite. J. Dent. Res. 62: 590–592.

Wilson–Hench, J. W., and Hench, L. L. (1985). Tissue response to surrface–active materials. In: McKinney, R. (Ed.) Dental Implants, Chapter 10.

Anusavice, Kenneth J. "Restorative Resins" *Phillip's Science of Dental Materials* (1996) $10^{th}$ ed. p. 278, W.B. Saunders Co.: Philadelphia.

Greenspan, David C. "Developments in Biocompatible Glass Compositions" *Medical Device & Diagnostic Industry* MDDI column (Mar. 1999).

Stanley, H.R., et al., "Implantation of Natural Tooth Form Bioglass in Baboons" *The International Journal of Oral Implantology* (1976/1977) 1(2): 30–47.

Stanley, H.R. "Pulp Capping: Conserving the Dental Pulp—Can it be Done? Is it Worth it?" *Oral Surgery, Oral Medicine, Oral Pathology* (1989) 68(5): 628–639.

Stanley, H.R. "Criteria for Standardizing and Increasing Credibility of Direct Pulp Capping Studies" *American Journal of Dentistry* Symposium Article (1998) 11: S17–S34.

McGraw–Hill *Dictionary of Scientific and Technical Terms* "Biocompatibility." Date unknown.

Guralnik, David B., editor in Chief *Webster's New World Dictionary of the American Language* $2^{nd}$ College Edition, Simon & Schuster, p. 54 & 1036. Date unknown.

\* cited by examiner

BIOACTIVE CERAMIC CEMENT

FIELD OF THE INVENTION

This invention relates to compositions and methods for enhanced fixation of implants to bone.

BACKGROUND OF THE INVENTION

Although acrylic bone cement (self-curing poly-methyl-methacrylate) (PMMA) has been the mainstay of total hip and knee fixation for over three decades, it is inert and does not form a bone bond. Rather, it induces the formation of a fibrous membrane, which separates the implant cement mantle from the approximating host bone. Accordingly, it has been recognized that PMMA merely forms a mechanical fixation, as opposed to a biological bond of tissue.

Despite many efforts to improve acrylic cement, the desired end result of increasing the longevity of implant fixation and decreasing aseptic loosening has, to date, not greatly changed the long-term prognosis of implant recipients treated with such cements.

In recent years, investigators have sought to move from "cement fixation" to "bioactive fixation" with bioactive materials such as hydroxyapatite, bioactive glasses or ceramics. Bioactive glass is a bioactive silica-structured glass that undergoes a corrosive chemical reaction of dissolution, leaching and precipitation when contacted with tissue (body) fluids, simulated body fluids (SBFs) or aqueous solutions which permit interaction of the bioactive glass with approximating cells and tissues. These chemical reactions promote the formation of a carbonate hydroxyapatite (HCA) layer upon the bioactive ceramic or glass core, which acts as an osseoconductive (bone forming stimulus) agent, and new bone formation bridges the gap between the implant and the adjacent host bone (osseointegration), thus forming a true biological bond. However, the disadvantage of known bioactive glass or other bioactive ceramic systems, even when mixed with appropriate resins, is that it takes months to produce enough new bone to achieve weight-bearing capacity. This is in contrast to the quick-fix-set of PMMA cement which at least provides in immediate weight-bearing capacity, even though as noted above, tending to fail in the long term.

SUMMARY OF THE INVENTION

The present invention provides a solution to the problems with known cements by providing a composition comprising (a) microscopic anhydrous pellets or particles containing the most important components of biological fluids or synthetic biological fluids (SBFs), (b) bioactive glass or other bioactive ceramic particles and (c) an appropriate resin such as, but not limited to, bisphenol-alpha-glycidyl methacrylate (BIS-GMA), to form a bone-forming cement which enhances (accelerates) bone production and bone bonding.

As a recipient's body or tissue fluids contact the components of the composition of this invention, a corrosive chemical reaction begins in which the anhydrous pellets or particles containing the components of biological fluids or SBF pellets are dissolved, thereby enhancing the corrosive chemical reaction at the surface of the bioactive glass or ceramic, and thereby accelerating a more uniform and significant amount of bone formation, not only on the surface of the cement mantle, but penetrating to a deeper level throughout the entire thickness of the mantle until the stem surface is reached. This process occurs in a continuous fashion over a period of time shorter than that typically required for bone infiltration when using bioactive glass or ceramic alone. The presence of anhydrous particles of biological fluids or SBFs, upon dissolution, produces voids into which bone cells easily migrate, until all the voids created by the dissolution of the pellets and the spaces between the resin particles are filled in with bone. This process is significantly different and superior to the quick initial cure and fixation set that occurs with PMMA cements, or the unacceptably long period of time required with bioactive glass or bioactive ceramic alone.

Accordingly, it is one object of this invention to provide a composition for rapidly and securely fixing an implant to a recipient's bone, while at the same time promoting autogenous bone infiltration into the cementous mantle about the implant.

A further object of this invention is to provide a method for rapidly and securely fixing an implant to a recipient's bone, while at the same time promoting autogenous bone infiltration into the cementous layer about the implant.

A further object of this invention is to provide a method for making and using a composition for rapidly and securely fixing an implant to a recipient's bone, while at the same time promoting autogenous bone infiltration into the cementous layer about the implant.

Further objects and advantages of this invention will be apparent from a review of the complete disclosure and claims appended hereto.

DETAILED DESCRIPTION OF THE PREFERRED EMBODIMENTS

Acrylic bone cement (e.g. self-curing poly-methylmethacrylate [PMMA]) has been used for about three decades for total hip and knee joint implant fixation with considerable success (Planell et al 1995). Its popularity is related to its fast initial fixation (quick curing set) which permits the patient to become ambulatory early and provides an effective load transfer from implant to bone (Lee et al 1997; Moreau et al 1998). However, as patients live longer, a worrisome percentage of them are experiencing aseptic loosening of their implants and consequently require repetitive revision surgery (Jonck et al 1989). The reason for this is that the PMMA cement is inert and does not bond with the adjacent bone but produces a thin fibrous membrane (0.1 to 1.5 mm thick) which indefinitely surrounds the cement mantle.

When PMMA cement polymerizes, high temperatures of up to 230° F. are created due to the exothermic nature of the reaction. Residual reactive monomers also remain at the implant site, and frequently produce irritation or other toxic effects. These two factors induce a zone of necrosis of up to about 3.0 mm wide in the implant bed (Planell et al 1995) which takes up to two years to replace (Willert et al 1974). Therefore, the retention of implants cemented with PMMA is mainly mechanical (Wilsôn-Hench and Hench; Stanley 1987).

Consequently many efforts have been made to improve the entire PMMA cementing system: to better ream and clean the bone cavity; to develop an air-driven cement gun to insert the cement under pressure (Fritsch 1996; Planell et al 1995); and to find alternative monomers, polymers, initiators and accelerators that are less toxic and which reduce the extent of the exothermic reaction and the undesirable temperature elevation of the surrounding tissue (Fritsch 1996; Lee et al 1997; Planell et al 1995 and Vazquez et al 1997). Some investigators have tried to either preheat or precool the stems of implants (Planell et al 1995) or to prechill the monomer (Walsh et al 1997). Some investigators have tried to make the set cement less rigid by increasing its porosity (Planell et al 1995; Willert et al 1974). Other investigators have incorporated metallic or polymeric fibers to reinforce the strength of the cement (Frigstad et al 1997).

In addition to trying to improve the cement, efforts have been made to make the stems of implants more amenable to mechanical retention with techniques to make the stem surface more irregular with grooves, ridges or beads (Morita et al 1997; Raab et al 1982). Roughness increases the surface area and the potential for increased bone-implant contact. It has even been proposed that these surface treatments would be so successful that the cement could be eliminated altogether (cementless implants). However, this concept has not met with as much long-term success as had been hoped for.

Implant stems have also been precoated with an adhesive acrylic bone cement containing methacryloyloxyethyl trimellitate anhydride (4-META) and MMA monomers which can then unite with the conventional bone cement as it polymerizes.

Despite all of these attempts to improve existing implant cements and implant methods, the basic problem of premature aseptic loosening of implants remains. The present invention addresses and overcomes many of these problems.

In recent years investigators have sought to move from pure "cement fixation" to bioactive materials such as hydroxyapatite (HA) and bioactive glasses (BG) which could induce "biological fixation" or "bioactive fixation" where the interface between implant and tissue develop a type of biologic (bony) bond (Hench 1998). The term "osseointegration" was introduced by Branemark (1983), who described the intimate contact between a titanium implant surface and the surrounding bone—a contact between normal and remodeled bone and an implant surface, without the interposition of connective tissue at the microscopic level (Gross et al 1997).

Those skilled in the art are familiar with various types of bioactive glasses or ceramics, including but not limited to a subgroup of surface-active silica-based synthetic biomaterials composed of minerals (Si, Ca, Na, $O_2$, H and P) which occur naturally in the body (Ogino et al 1980). The main component of bioactive glasses is a 3-dimensional silica network ($SiO_2$) (Andersson et al 1993; Stanley 1995). Such compositions are useful for inclusion in the composition of the present invention in the form of particles or pellets, as further outlined below.

Certain glasses are called "active" because when they are contacted by body (tissue) fluids, SBFs or aqueous solutions, they undergo dissolution, leaching and precipitation (Andersson et al 1993; Stanley 1995) and interact actively with approximating cells and tissue to produce bone which bonds to the adjacent host bone (Hench 1991). However, this phenomenon only occurs if the bioactive glass is situated within about 0.5 mm of approximating vital compact bone (Harrell et al 1978). The BIOGLASS® formula 45S5 is a very active bone inducer, many times more active than HA (Hench 1991). Use of such a bioactive glass, and variants thereof, is preferred according to the present invention.

When the silica structured network on the surface of a bioactive glass implant comes in contact with the appropriate fluids, the hydrogen ions from the body fluids replace the $Na^+$ ions in the glassy network which are released into the solution (Andersson and Kangasniemi 1991; Hench 1981; Hench & Paschall 1974; Ogino et al 1980 and Stanley et al 1997). This reaction produces hydroxyl ions which leads to a dissolution or breakdown of the silicon-oxygen bonds (Si—O—Si) to form silanols (Si—OH) on the surface of the bioactive glass or other ceramic. This then permits Ca and $PO_4$ ions within the implant to migrate to its surface (leaching). The surface silanols then condense and repolymerize, creating a hydrated silica-rich layer. The Ca and $PO_4$ ions that leach at the beginning of the tissue fluid contact are also reprecipitated, but on top of the silica-rich layer to begin the formation of a carbonate hydroxyapatite (HCA) layer. Usually, for a bioactive glass implant material to bond to living bone, the material must have the ability to form a carbonate containing hydroxyapatite (HCA) layer on its surface. Some researchers refer to this layer simply as a calcium phosphate (CaP) layer. This layer bridges the implant material to the host tissue. The newly formed silica-rich layer has a gel-like consistency, and provides an energetically favored pathway for attracting and incorporating additional Ca, $PO_4$, and $CO_3$ (carbonate) ions from body fluids to enhance formation of the HCA layer. The HCA layer then acts as an osseo-conductive agent guiding the location for new bone formation. When this occurs near host bone, new bone firmly attaches to the HCA layer. (Andersson et al 1993a; Andersson et al 1993b; Filguerias et al 1993; Hench 1981; Hench 1991; Hench & Ethridge 1981; Kim et al 1993; Li et al 1993; Radin et al 1997; Stanley 1987; Stanley 1995; West and Hench 1993). The silica-rich gel layer is about 200 $\mu$m thick and can be divided into two zones: an inner zone, closer to the bulk or core of bioactive glass, which is a silica rich layer approximately 120 $\mu$m in width, and an outer Ca, $PO_4$ rich zone (HCA layer), approximately 70 $\mu$m in width, which lies between the Si-rich layer and the new bone (Clark et al 1979; Hench & Clark 1982; Stanley 1995 and Stanley 1987). Hench & Ethridge (1982) proposed that the gel bonding layer results in a gradient of elastic compliance (springiness; functional ankylosis) which mimics a natural junctional interface between hard and soft tissue, thereby permitting a favorable stress (load) transfer from the implant to the newly formed bone, much like a natural tooth surrounded by a periodontal ligament (Clark et al 1979; Gross et al 1997; Hench & Clark 1982; Stanley et al 1987 and Weinstein et al 1980). This proposal is supported by the observation that the elastic modulus gradient between an HCA implant and bone is nearly 1000 times higher than the gradient between BIOGLASS® and bone (Hench & Ethridge 1982). This explains why fractures occur either within the implant itself or in the newly formed surrounding bone, but not at the interface (Piotrowski et al 1975 and Stanley et al 1976). The interface region induced by the bioactive glass acts as a shock absorber, minimizing the transmission to bone of tension and compressive forces when a mechanical load is applied to the implant (James 1984 and Weinstein et al 1980). While HA materials and bioactive glasses have been mixed with resin to form cements or applied as coatings to stems, there remains the need to extend the efficiency by which the HCA layer is formed. The present invention accomplishes this goal by including anhydrous pellets of biological fluid components or components of synthetic biological fluids into a composition including the bioactive glass or ceramic, such that upon hydration, the degree of HCA layer formation is maximized.

To improve a dental filling material (silicate cement), a material called "glass ionomer cement" (GIC) was invented when Wilson & Kent (1971) mixed polyacrylic acid (PAA), instead of phosphoric acid, with the aluminosilicate glass of a dental silicate cement. The original GIC consisted of:

$SiO_2$, $Al_2O_3$, $AlF_3$, $CaF_2$, NaF and $AlPO_4$ (Wilson & McLean 1988). Wilson et al (1983) noted the development of a layer at the interface between dentin and the GIC consisting of Ca & $PO_4$ ions. The GIC bonded chemically to dentin without any preconditioning and without forming bone. This resulted from the chemical reaction when the PAA attacks the aluminosilicate glass particles. The H ions associated with the acidic solution erodes the surface of the glass powder (particles) and releases Na, Ca, and Al. These ions migrate into an aqueous phase to form a hydrated siliceous gel about the remaining glass core (Wilson & Prosser 1982). As the reaction proceeds, the original hydrogen bridges are progressively replaced or added to by stronger Ca & Al bridges (Wilson 1977). To speed up the reaction (to make it harden quicker) tartaric, itaconic, maleic and mesaconic acids were added (Nicholson et al 1988; Wilson & Kent 1971; Wilson 1978 and Prosser et al 1982).

The glass and the reaction acids when first mixed are initially slightly toxic but as the mixture (cement) cures, the toxicity decreases. GICs have been used for the cementation of orthopedic implants but with rather poor results, even short term. For dentistry, it was decided to create an anhydrous form of GIC because dentists were unable to master the mixing of the components in their proper ratio.

Wilson & Kent (1973) used the various acids in a dry powder form blended with glass-ionomer powder. The cement was then formed by mixing the blend of powders with water. All the dentist needed to do was add water or a dilute acid (tartaric acid) and produce the most favorable chemical reaction for a stronger, longer lasting filling material. One can see here a similarity between the chemical reactions of bioactive glasses when exposed to fluids (water, serum, SBFs) and the anhydrous GICs when exposed to water or tartaric acid.

When Tamura et al (1995) replaced the PMMA with bisphenol-alpha-glycidyl methacrylate resin (BIS-GMA) and added a bioactive glass powder, they found the compressive strength to be much higher with direct contact between implant material and bone, without intervening fibrous tissue. However, it took 6.5 months in rat tibias to reach a load-bearing capability (LBC). Nevertheless, their work represented a breakthrough in the use of bioactive glass. They showed that the formula, despite the presence of resin, still induced an apatite (HCA) layer and a Si-rich layer between the resin particles as described by Clark et al (1979) and Hench & Clark (1982). They also demonstrated that the cement permitted infusion of tissue fluid into the cement and formed bone at the outer surface of the cement mantle just like a solid piece of bioactive glass undergoing chemical erosion. They showed that the cement layer itself was transformed and became part of the bony union with the approximating host-bone. No intervening fibrous tissue developed between the host-bone and the cement, as the entire composition all became one bonded unit over an extended time period.

In spite of the advances achieved by Tamura et al., (1995), the need remains to speed up the formation of bone in human and animal implants to enhance total joint implant fixation, especially in older patients or animals. Bioactive glasses and other ceramics, including but not limited to hydroxyl apatite, other calcium phosphate ceramics or BIOGLASS®, have many attributes as bioactive materials. They don't induce bone necrosis, they are non-toxic and are simply activated by body (tissue) fluids on contact. Many of such known materials don't induce extreme exothermic temperatures, they induce proliferation of osteoblasts of the most differentiated histologic phenotype at the highest rate and increase alkaline phosphatase activity to a greater extent than any other known bioactive material, (Vrouwensvelder et al 1993), without the need to add bone morphogenetic proteins. Sufficient quantities of such hormones are typically sequestered and are released from adjacent host bone or newly formed osseoconductive bone to carry on the process. It is also known that cell adhesion to extracellular matrices or to implant surfaces is required of osteoblastic progenitor cells to become osteoblasts capable of producing significant quantities of new bone (Lobel & Hench 1998). The adsorption of proteins such as fibronectin, poly-D-lysine, lamina, Type I and II collagen, serum and albumin enhance this process through the reaction of bioactive glasses with tissue fluids, producing an outer surface coating of an HCA layer, which is most elegant for attracting these proteins (Lobel & Hench 1998; Gainey et al 1998). It is further known that bioactive glass particles above a certain size are not stimulators of phagocytosis (macrophages and foreign body giant cells). Furthermore, bioactive glasses provide a bony attachment without intervening fibrous tissue. In spite of all of these advantages, the major drawback of bioactive glasses and other ceramics is the length of time for the bone to form around the implant to match the fixation equivalent of an implant cemented with acrylic. Despite the excellent features of bioactive glasses, as compared to PMMA cement, it still takes months to produce enough bone to provide a weight-bearing capacity.

The present invention solves the limitations encountered with bioactive glasses and other ceramics by providing compositions comprising bioactive glasses or other ceramics with a powdered or particulate form of activators, such as biological fluid components or components of SBFs, to speed up bone formation. As the tissue fluids interact with the closest bioactive glass particles, such powdered "activators" according to this invention come into play to reach the less accessible bioactive glass particles, thereby bringing about a greater and more uniform release of appropriate ions to enhance osseoconduction.

According to the present invention, SBF containing $Na^+$, $K^+$, $Mg^{2+}$, $Ca^{2+}$, $Cl^-$, $HCO_3^-$, $SO_4^{2-}$, $HPO_4^{2-}$ ions and pure $H_2O$ or TBS (tris-hydroxymethyl aminomethane) containing $[(CH_2OH)_3 \ CNH_2.]$ HCl and $H_2O$ (Kim et al 1993), are preferred for producing anhydrous particles for inclusion in the composition of this invention to enhance bone formation using bioactive glasses or other ceramics. Dissolution of bioactive glasses in SBFs has been observed (see, for example, Abe et al 1990; Filgueiras et al 1993; Hench & Clark 1982; Kangasniemi et al 1993; Kim et al 1993; Kokubo et al 1990; Le Geros et al 1978; Li et al 1992; Li et al 1993, Li et al 1997 and Lu et al 1997; Ogino et al 1980; Pantano et al 1974 and Vrouwenovelder et al 1993). It is apparent that the concentration of the ingredients of the SBFs and the consequent pH of the environment (that is the reacting solution) have an effect on bioactive glass particles in terms of the rate (speed) and degree of leaching (corrosion behavior) in the development of a silica-rich layer (a silica hydrogel) and an HCA layer. Whatever the conditions, the silica component must be readily hydrolyzed to produce sufficient silanol groups for the induction of apatite nucleation.

Thus, according to the present invention, anhydrous (dried-without water) ingredients of biological fluids or SBFs are included in pellets or particles, for implantation with bioactive glass or ceramic particles. The anhydrous particles or pellets containing components of biological fluid SBFs consist of ingredients commonly used in different SBFs (Filguerias et al 1993; Kim et al 1993 and Kokubo et al 1991). Those skilled in the art will further appreciate that with specific testing, some of the ingredients of biological fluids of SBFs could be eliminated, without compromising the ability of the composition to induce rapid bone bonding with implant surfaces.

The essential anhydrous components of biological fluids or SBFs are compressed into microscopic pellets or particles to enhance corrosion of bioactive glasses or ceramics upon co-implantation. Upon implantation, most of the inserted cement of the present invention containing a resin, bioactive glass particles and the anhydrous corrosion enhancing composition sets up initially and sufficiently to fix the implant. Once the cement is in position, the chemical reaction progresses indefinitely after the initial setting. This is in sharp contrast to the situation when PMMA cement is used, since PMMA sets up quickly, with acceptable mechanical properties for a few months, followed by a long term degradation process (Planell et all 995). According to the process of the present invention, an initial bulk (mantle) of bioactive glass cement sets, simulating the strength achieved using a conventional cement, such as PMMA. Then, over time, the bioactive glass particles and anhydrous corrosion enhancing pellets or particles of this invention on the surface of the mantle that first come in contact with the tissue fluid transuding from the approximating original host tissues (bone) are dissolved, and are activated and respond with the typical chemical reaction that leads to new bone formation. Once the outer peripheral surface of the cement mantle is transformed to bone, the bioactive glass particles and corrosive pellets in the next deeper levels (increments) of the cement mix are activated through contact with tissue fluids released from the newly formed bone containing built-up sequestered bone growth factors (bone morphogenetic proteins). As this process continues, the deeper and deeper bioactive glass particles and pellets are converted into active-corroding agents which eventually transform the entire thickness of the cement mantle with bone until reaching the outer surface of the implant stem. As the bioactive glass particles and pellets are activated and dissolved the resulting voids or spaces that result are adequate to permit the ingrowth of the necessary vascular tissue to support the next increment of bone formation. The anhydrous components within the pellets and the cement mix at the deepest levels approaching the stem interface remain indefinitely available to be activated, without losing the capacity for chemical reaction to lead to osseoconductive bone formation.

As Stanley (1987) and Steflik et al (1998) have pointed out, collagen fibers already present or developing (an unmineralized collagen fiber matrix) at the implant-bone interface are subsequently mineralized during osteogenesis. In the presence of this unmineralized collagen fiber matrix, osteoblasts in the area begin to deposit foci of mineralization not only about the collagen fibers but also around their own (osteoblast) cellular processes. As these processes become entrapped, the osteoblasts become osteocytes. These extending processes almost touch the implant stem surface (within 20 nanometers) and some splay and then run parallel to the implant surface providing channels (canaliculi) for the permeation of tissue fluids from nearby vascular sources (Steflik et al 1998).

The anhydrous SBF pellets included in the composition of this invention, by enhancing the chemical reactions of bioactive glasses with bone tissue, bring about a greater and more uniform release of the appropriate ions needed to speed up the formation of apatite (the HCA layer) and bone formation.

BIOGLASS® has one tremendous advantage over other similar products. When the fracture line of a BIOGLASS® implant occurs within living tissue, new bone is deposited on the freshly exposed surface, irrespective of the postoperative implant interval, just as when first implanted. Such surfaces become completely covered with new bone. In other words, when a fresh surface of BIOGLASS® appears, in this case due to a fracture, the osteoconductive activity is reinitiated, just as it was when first implanted. This is the opposite to fatigue fractures encountered with other implant materials, which can leave distorted, ragged metal fragments to work their way out of the tissue. It is possible that BIOGLASS® is the only known implant material that can heal itself (Stanley et al 1981; Stanley et al 1987). Thus, while it is difficult to speed up the actual formation of osteoblasts or increase their production of osteoid tissue, with the composition of the present invention, those skilled in the art are enabled to stimulate a more uniform production of osteoblasts and consequently more bone.

Use of the composition of the present invention eliminates the need to incorporate bone growth factors (bone morphogenetic proteins) into the cement, because bioactive glass already performs very well in the stimulation and production of osteoblasts, maximizing phenotype osteoblast development, and the rate of increase in alkaline phosphatase activity (Vrouwensvelder et al 1993). Nonetheless, inclusion in the composition of this invention of various growth factors, including but not limited to bone morphogenetic protein, other growth factors, nucleic acids and the like, is not excluded, and in certain circumstances, may be desirable.

Although bioactive glass does not require a roughened surface, grooves, or beads, since in its gelatinous state it fills in all nearby irregularities, it is sometimes advantageous to have some deep grooves on the stem surface large enough to support the growth of bone. Principally, however, according to the method and composition of the present invention, inclusion of microscopic pellets or particles enhances corrosion of the adjacent bioactive glass particles when contacted by tissue fluid. The approaching tissue fluid releases the appropriate elements from the pellet and initiates the corrosive reaction. If increased stability of hip/knee implants is needed to reduce surface wear and the production of wear particles and aseptic loosening, the bioactive glass cement of the present invention provides actual bone bonding through osteoconduction and a gradual transformation of the entire thickness of the cement mantle. This results in a greater amount of bone ingrowth into the cement mantle during the early post-operative periods, which enhances long-term fixation.

Accordingly, this invention provides a composition comprising: (a) bioactive glass, bioactive ceramic or both; (b) anhydrous particles which contain the components of a biological fluid or an anhydrous particle which contains the components of a synthetic biological fluid; and (c) a biocompatible resin. Preferably, the anhydrous biological fluid or said anhydrous synthetic biological fluid comprises $Na^+$ ions, $K^+$ ions, $Mg^{2+}$ ions, $Ca^{2+}$ ions, $Cl^-$ ions, $HCO_3^-$ ions, $SO_4^{2-}$ ions, $HPO_4^{2-}$ ions, and combinations thereof. Optionally, these ions are dispersed in (tris-hydroxymethyl aminomethane), and in one embodiment of this invention, the biocompatible resin is bisphenol-alpha-glycidyl methacrylate.

As is known in the art, bioactive glass comprises Si, Ca, Na, $O_2$, H and P, although it is preferred that the bioactive glass used in the method and composition of this invention is 45S5 bioactive glass such as BIOGLASS®.

Preferably, the components of the composition of this invention are intimately blended into a mixture of the (a) bioactive glass, bioactive ceramic or both; (b) anhydrous biological fluid or anhydrous synthetic biological fluid; and (c) biocompatible resin, such that the composition may be implanted into a recipient in need thereof without the need for measuring components at the time of implantation. Accordingly, in a preferred embodiment, the composition of this invention comprises a bioactive glass, anhydrous components of a biological fluid or anhydrous components of a synthetic biological fluid comprising $Na^+$ ions, $K^+$ ions, $Mg^{2+}$ ions, $Ca^{2+}$ ions, $Cl^-$ ions, $HCO_3^-$ ions, $SO_4^{2-}$ ions, and $HPO_4^{2-}$ ions, and bisphenol-alpha-glycidyl methacrylate. When the biocompatible resin is a liquid, the intimate admixture with the anhydrous particles of bioactive glass and biological or synthetic biological fluid components forms a readily implantable paste or slurry. The paste or slurry thus formed may be used to coat the surface of an implant or it may simply be used to coat an implant site or both.

Desirably, the particles of bioactive glass or ceramic, and the anhydrous particles containing components of a biological fluid or SBF have an average size in the range between about 90 $\mu$m and about 1000 $\mu$m, or between about 150 $\mu$m and about 250 $\mu$m. In addition, as noted above, the composition according to this invention may further include growth factors, hormones, proteins, peptides, nucleic acids, and combinations thereof.

Those skilled in the art will recognize that the composition of this invention may be used to induce bone formation about an implant by contacting a bone implant site and an implant with a composition comprising (a) bioactive glass, bioactive ceramic or both; (b) anhydrous particles which contain the components of a biological fluid or anhydrous particles which contain the components of a synthetic biological fluid; and (c) biocompatible resin.

Having now described this invention is considerable detail, including the best mode and the methods of making the composition of this invention and the methods of use thereof, it will be appreciated that exclusive rights in this invention should not be considered to be limited to the specifics as taught herein. Rather, it should be understood that the invention in which exclusive rights are claimed herein is defined by the elements of the following claims, and equivalents thereof.

References

While the following references may be mentioned in the text of this disclosure, this should not be taken as an indication that any of these references are considered to be of any particular relevance to the patentability of the claims appended hereto:

Andersson, O. H., and Kangasniemi, L. (1991). Calcium phosphate formation at the surface of bioactive glass in vitro. J. Biomed. Mater. Res., 25, 1019–1030.

Andersson, O. H., Karlsson, K. H., Kangasniemi, K., and Yli-Urpo, A. (1988). Models for physical properties and bioactivity of phosphate opal glasses. Glastech. Ber., 61, 300–305 (quoted by Andersson et al, 1993).

Andersson, O. H., La Torre, G., and Hench, L. L. (1992). "The kinetics of bioactive ceramics. Part II: Surface reactions of three bioactive glasses." in Bioceramics, Vol 3, E. J. Hulbert and S. F. Hulbert (eds.), Rose-Hulman Press. Quoted by Filgueiras et al 1993.

Andersson, O. H., Liu, G., Karlsson, K. H., Niemi, L., Miettinen, J., and Juhanoja, J. (1990). In vivo behavior of glasses in the $SiO_2$—$Na_2O_2$—$CaO$—$P_2O_5$—$Al_2O_3$—$B_2O_3$ system. J. Mater. Sci.: Mater. Med., 1, 219–227.

Andersson, O. H., Rosenqvist, J., and Karlsson, K. H. (1993). Dissolution, leaching, and $Al_2O_3$ enrichment at the surface of bioactive glasses studied by solution analysis. J. Biomed. Mater. Res., 27, 941–948.

Branemark, P-I. (1983). "Osseointegration and its experimental background". J. Prosthet. Dent. 50: 399–410. (Quoted by Gross et al 1997).

Clark, A. E., Pameijer, C. H., and Stanley, H. R. (1996). "Bioglass® as a pulpcapping agent". J. Dent. Res. 75 Special Issue. Abstract #2104, p. 280.

Clark, A. E., Jr., Stanley, H. R., Acree, W. A., and Kreutziger, K. (1979). Thickness of bonding layers on Bioglass® dental implants. J. Dent. Res., 58, Special Issue A, Abstract 824.

Filgueriras, R. M., La Torre, G., and Hench, L. L. (1993). Solution effects on the surface reactions of a bioactive glass. J. Biomed. Mater. Res., 27, 445–453.

Frigstad, J. R., Kang, Y. H., and Park, J. B. (1997). "Reinforcement of PMMA bone cement with a continuous wire coil: a canine implantation study". Transactions of Society for Biomaterials, New Orleans, La., Apr. 30–May 4, p. 239.

Fritsch, E. W. (1996). "Static and fatigue properties of two new low-viscosity PMMA bone cements improved by vacuum mixing". J. Biomed. Mater. Res. 31: 451–456.

Gainey, G. M., Landesberg, R. L., and Katz, R. W. "Binding of osteoblast cell lines to extracellular matrix proteins". J. Dent Res. (1998) 77 Special Issue A, Abstract #861, p. 213.

Gross, K. A., Berndt, C. C, Goldschlag, D. D., and Iacono, V. J. (1997). "In vitro changes of hydroxyapatite coatings". Int. J. Oral Maxillofac. Implants 12: 589–597.

Harrell, M. S., Keane, M. A., Acree, W. A., Bates, S. R., Clark, A. E., and Hench, L. L. (1978). Thickness of Bioglass bonding layers. Trans 4 th Annual Meeting Society for Biomaterials, San Antonio, Tex., p. 111.

Hench, L. L. (1980). The interfacial behavior of biomaterials. J. Biomed. Mater. Res., 14,805–811.

Hench, L. L. (1981). Stability of ceramics in the physiological environment. In Fundamental Aspects of Biocompatibility (D. F. Williams, ed.), Vol. 1, CRC Press, Boca Raton, Fla., pp. 67–85.

Hench, L. L. (1991). Bioceramics: From concept to clinic. J. Am. Ceram. Soc., 74, 1487–1510.

Hench, L. L. (1998). "Bioactive materials, the potential for tissue regeneration". J. Biomed. Mater. Res. 41: 511–518.

Hench, L. L. (1998). "Bioactive ceramics." In: Ducheyne, P., and Lemmons, J. E. (eds). Bioceramics: Materials Characteristics Versus in vivo Behavior Annals of the New York Academy of Sciences. N. Y.: New York Academy of Sciences, 1988;523: 54–71.

Hench, L. L., Andersson, O. H. and La Torre, G. P. (1991). "The kinetics of bioactive ceramics. Part III: Surface reactions for bioactive glasses compared with an inactive glass". Bioceramics, Vol 4, W. Bonfield, G. W. Hastings and K. E. Tanner (eds.). Butterworth-Heinemann Ltd., Guildford, England pp: 155–162. Quoted by Filgueiras et al 1993.

Hench, L. L., and Clark, A. (1982). Adhesion to bone. In Biocompatibility of Orthopedic Implants (D. F. Williams, ed.), Vol. 2. CRC Press, Boca Raton, Fla., Chap. 6. pp. 129–170. (Quoted by Jonck et al 1989 [Clinical Mats 4: 85–107]).

Hench, L. L., and Ethridge, E. C. (1982). Biomaterials: An Interfacial Approach. Academic Press, New York, Chaps. 5, 7, 14.

Hench, L. L., Greenlee, T. K., Jr., and Allen, W. C., (1970). An investigation of bonding mechanisms at the interface of a prosthetic material. Annual Report No. 1, U.S. Army Med. Res. Dev. Contract No. DADA-17-70-C-0001.

Hench, L. L., and Paschall, H. A. (1973). "Direct chemical bond of bioactive glass-ceramic materials to bone and muscle." J. Biomed. Mater. Res., Symp. 4: 25–42.

Hench, L. L., and Paschall, H. A. (1974). Histochemical responses at a biomaterial's interface. J. Biomed. Mater. Rels., 3, 49–64.

Hench, L. L., Splinter, R. H., Allen, W. C., and Greenlee, T. J. (1972). "Bonding mechanisms at the interface of ceramic prosthetic materials". J. Biomed. Mater. Res. 5: 117–141.

James, R. (1984). Tissue response to dental implant devices. In Clinical Dentistry, Vol. 5 (J. W. Clark, ed.). Harper & Row, Philadelphia, Chap. 48, pp. 8–9.

Jonck, L. M., Grobbelaar, C. J. and Strating., H. (1989). "The biocompatibility of a glass-ionomer cement in joint replacement: bulk testing". Clinical Mater. 4: 85–107.

Jonck, L. M., Grobbelaar, C. J. and Strating, H. (1989). "Biological evaluation of glass-ionomer cement (Ketac-O) as an interface material in total joint replacement. A screening test". Clin. Mater. 4: 201–224.

Kangasniemi, I. M. O., Vedel, E., de Blick-Hogerworst, J., Yli-Urpo, A. U., and de Groot, K. (1993). Dissolution and scanning electron microscopic studies of Ca, P particle-containing bioactive glasses. J. Biomed. Mater. Res., 27, 1225–1233.

Kim, C. Y., Kim, J., and Chang, S. Y. (1993). Hydroxyapatite formation on bioactive glass in a solution with different pH and P-ion concentration. Trans. 19 th Annual Meeting Soc. Biomaterials, April 28–May 2, Birmingham, Alabama, p. 4.

Kokubo, T. (1990). Surface chemistry of bioactive glass-ceramics. J. Non-Cryst. Solids, 120, 138–151 (quoted by Hench, 1991).

Kokubo, T. (1991). Bioactive glass-ceramico-properties and applications. Biomaterials, 12, 156–163 (quoted by Kangasniemi et al., 1993).

Kokubo, T., Kushitani, H., Sakka, S., Kitsugi, T. and Yamamuro, T. (1990). "Solution-sable to reproduce in vivo surface-structure changes in bioactive glass-ceramic A-W." J. Biomedical Materials Research, 24: 721–734. (Quoted by Filgueriras et al 1993).

Kokubo, T., Yoshihara, N., Nishimura, T., Yamamuro, T., and Nakamura, T., 1991, Bioactive bone cement based on $CaO—SiO_2—P_2O_5$ glass. J. Am. Ceram. Soc 74: 1739.

Lee, R. R., Ogiso, M., Watanabe, A., and Ishihara, K. (1997). "Examination of hydroxyapatite filled 4-META/MMA-TBB adhesive bone cement in in vitro and in vivo environment". J. Biomed. Mater. Res. (Appl Biomater.) 38: 11–16.

LeGeros, R. F., Bone, G., and LeGeros, R. (1978). Type of $H_2O$ in human enamel and in precipitated apatites. Calcif. Tissue Res., 26, 111 (quoted by Hench, 1991).

Li, P., Bakker, D., and van Blitterswijk, C. A. (1997). "The bone-bonding polymer Polyactive® 80/20 induces hydroxycarbonate apatite formation in vitro". J. Biomed. Mater. Res. 34: 79–86.

Li, P., Ohtuski, C., Kokubo, T., Nakanishi, K., and Soga, N. (1992). Apatite formation induced by silica gel in a simulated body fluid. J. Am. Ceram. Soc., 75, 2094–2097 (quoted by Kangasniemei et al., 1993).

Li, P., Ohtsuki, C., Kokubo, T., Nakanishi, K., Soga, N., Nakamura, T., and Yamamuro, T. (1993). Effects of ions in aqueous media on hydroxyapatite induction by silica gel and its relevance to bioactivity of bioactive glass and glass-ceramics. J. Appl. Biomat., 4, 221–229.

Li, P., Qui, Q., and Ducheyne, P. (1997). "Surface transformation of titanium to apatite affecting mineralization of extracellular matrix in rat marrow stromal cell culture". Transactions of Society for Biomaterials, New Orleans, La., Apr. 30–May 4, p. 384.

Lobel, K. D., and Hench, L. L. (1996). "In vitro protein interactions with a bioactive gelglass". J. Sol-Gel Sci. Technol., 7, 69–76 (Quoted by Hench 1998. "Bioactive materials: The potential for tissue regeneration". J. Biomed. Mater. Res. 41: 511–518.

Lu, H-Y., Helen, Pollack, S. R., and Ducheyne, P. "Relationship between surface charge and the formation of a calcium phosphate layer on bioactive glass in vitro". Transactions of Society for Biomaterials, New Orleans, La., Apr. 30–May 4, 1997, p. 126.

Lu, X., Topoleski, L. D. T., and Neerchal, N. K. "The influence of notch tip geometry on fatigue crack initiation in PMMA bone cement". Transactions of Society for Biomaterials, New Orleans, La., Apr. 30–May 4, 1997, p. 235.

Moreau, M. F., Chappard, D., Lesourd, M., Montheard, J. P., and Basle, M. F. (1998). "Free radicals and side products released during methylmethacrylate polymerization are cytotoxic for osteoblastic cells". J. Biomed. Mater. Res. 40: 124–131.

Morita, S., Yamamoto, H., Furuya, K., Ishihara, K., and Nakabayashi, N. (1997). "Enhanced strength in cemented stem fixation using adhesive acrylic cement as a metal coating material." J. Biomed. Mater. Res. 34: 171–175.

Nicholson, J. W., Brookman, P. J., Lacy, O. M., and Wilson, A. D., (1988). Fourier transform infrared spectroscopic study of the role of tartaric acid in glass-ionomer dental cements. J. Dent. Res. 67: 1451–1454.

Ogino, M., and Hench, L. L. (1980). Formation of calcium phosphate films on silicate glasses. J. Non-Cryst. Solids, 38–39, 673–378.

Ogino, N., Ohuchi, F., and Hench, L. L. (1980). Compositional dependence of the formation of calcium phosphate fibers on Bioglass®. J. Biomed. Mater. Res., 14, 55–64 (quoted by Hench, 1991).

Pantano, C. G., Jr., Clark, A. E., Jr., and Hench, L. L. (1974). Multilayer corrosion films on glass surfaces. J. Am. Ceram. Soc., 57, 412–413.

Piotrowski, G., Hench, L. L., Allen, W. C., and Miller, G. J. (1975). Mechanical studies of the bone bioglass interfacial bond. J. Biomed. Mater. Res., 6, 47–61 (quoted by Hench and Ethridge, 1982).

Planell, J. A., Vila, M. M., Gil, F. J., and Driesseny, F. C. M. (1995). "Acrylic bone cements". In Encyclopedic Handbook of Biomaterials and Bioengineering, Part B: Applications, Vol. 2, Chapter 32, pp. 879–921. Edit by D. L. Wise et al, Marcel Dekker, Inc., New York.

Prosser, H. J., Richards, C. P. and Wilson, A. D. (1982). "NMR Spectroscopy of Dental Cements, II. The role of tartaric acid in glass-ionomer cements". J. Biomed Mater. Res. 16:431–445. (Quoted by Nicholson et al 1988).

Raab, S., Ahmed, A. M., and Provan, J. W. (1982). "Thin film PMMA precoating for improved bone-cement fixation". J. Bone Joint Surg. [Br.], 71: 217–221. (Quoted by Morita et al 1997).

Radin, S., Ducheyne, P., and Falaize, S. (1997-A). "Sol-gel-derived glass (SG) with a controlled surface reactivity". Transactions of Society for Biomaterials, New Orleans, La., Apr. 30–May 4, 1997, p. 161.

Radin, S., Ducheyne, P., Reicin, K. E., and Lee, M. H. (1997-B). "The effect of composition and in vitro immersion on the formation of a bioactive surface on sol-gel derived glass". Transaction of Society for Biomaterial, New Orleans, La. Apr. 30–May 4, p.340.

Stanley, H. R., (1987). Implantology and the development of Bioglass. In The 1987 Dental Annual (D. D. Derrick, ed.). John Wright & Sons, Bristol, pp. 209–230.

Stanley, H. R. (1995). "Alveolar ridge maintenance using endosseously placed Bioglass® (45S5) cones". Encyclopedic Handbook of Biomaterials and Bioengineering, Part B: Applications Volume 2: 1559–1616, Ed. by D. L. Wise et al. Marcel Dekker, Inc. New York.

Stanley, H. R., Hall, M. B., Clark, A. E., King, C. J. III., Hench, L. L., and Berte, J. J. (1997). "Using 45S5 Bioglass cones as endosseous ridge maintenance implants to prevent alveolar ridge resorption: A 5-year evaluation." Int. J. Maxillofac Implants 12: 95–105.

Stanley, H. R., Hall, M. B., Colaizzi, F., and Clark, A. E. (1987). Residual alveolar ridge maintenance with a new endosseous implant material. J. Pros. Dent., 58, 607–613.

Stanley, H. R., Hench, L. L., Bennett, C. G., Jr., Chellemi, S. J., King, C. J., III, Going, R. E., Ingersoll, N. J., Ethridge, E. C., Kreutziger, K. L., Loeb, L., and Clark, A. E. (1981). The implantation of natural tooth form Bioglass in baboons—Long term results. Int. J. Oral Implant, 2, 26–38.

Stanley, H. R., Hench, L. L., Going R., Bennett, C., Chellemi, S. J., King, C. J, III, Ingersoll, N., Ethridge, E., and Kreutziger, K. (1976). The implantation of natural tooth form Bioglasses in baboons: A preliminary report. Oral Surg Oral Med Oral Pathol 1976; 42: 339–356.

Steflik, D. E., Corpe, R. S., Lake, F. T., Young, T. R., Sisk, A. L., Parr, G. R., Hanes, P. J., and Berkery, D. J. "Ultrastructural analyses of the attachment (bonding) zone between bone and implanted biomaterials". J. Biomed. Mater. Res. 39: 611–620.

Tamura, J., Kawanabe, K., Yamamuro, T., Nakamura, T., Kokubo, T., Yoshihara, S., and Shibuya, T. (1995). "Bioactive bone cement: the effect of amounts of glass powder and histologic changes with time". J. Biomed. Mater. Res. 29: 551–559.

Vazquez, B., Elvira, C., Levenfeld, B., Pascual, B., Goni, I., Gurruchaga, M., Ginebra, M. P., Gil, F. X., Planell, J. A., Liso, P. A., Rebuelta, M., and San Roman, J. (1997). "Application of tertiary amines with reduced toxicity to the curing process of acrylic bone cements." J. Biomed. Mater. Res. 34: 129–136.

Vrouwenvelder, W. C. A., Groot, C. G., and de Groot, K. (1993). Histological and biochemical evaluation of osteoblasts cultured on bioactive glass, hydroxylapatite, titanium alloy, and stainless steel. J. Biomed. Mater. Res., 27, 465–475.

Walsh, H. A., McCabe, J. P., Parks, M. L., Wright, T. M., Salvati, E. A., and Li, S. "Effect of altered polymarization rate on the mechanical properties of two brands of bone cement". Transactions of Society for Biomaterials, New Orleans, La., April 30–May 4, 1997, p.398.

Weinstein, A. M., Klawitter, J. J., and Cook, S. D. (1980). Implant-bone characteristics of Bioglass dental implants. J. Biomed. Mater. Res., 14, 23–29.

West, J. K., and Hench, L. L. (1993). Molecular orbital modeling of bioactive glass reactions of stages 3 and 4. Trans. 19th Annual Meeting Soc. Biomaterials, Birmingham, Ala., p. 2 (abstract).

Willert, H. G., Ludwig, J., and Semlitsch, M. (1974). "Reaction of bone to methacrylate after hip arthroplasty". The Journal of Bone & Joint Surgery 56-A, No. 7, October 1974, pp. 1368–1382.

Wilson, A. D., (1977). The development of glass-ionomer cement? Dent. Update (Oct.): 401–412.

Wilson, A. D. (1978). "The chemistry of dental cements". Chem. Soc. Rev. 7: 255–296. (Quoted by Nicholson et al 1988).

Wilson, A. D., and Kent, B. E. (1971). The glass-ionomer cement, a new translucent dental filling material. Jrl. of Applied Chemistry and Biotechnology 21: 313–318.

Wilson, A. D., and Kent, B. E., (1973). Surgical cement Brit. Pat. No. 1. 316, 129.

Wilson, A. D. and McLean, J. W. (1988). "Glass-ionomer cement". Quintessence Publishing Co., Inc. Chicago.

Wilson, A. D., and Prosser, H. J., (1982). Biocompatibility of the glass-ionomer cement. J. Dent. Assoc. S. Afr. 37: 872–879.

Wilson, A. D., Prosser, H. J., and Powis, D. R. (1983). Mechanism of adhesion of polyelectrolyte cements to hydroxyapatite. J. Dent. Res. 62: 590–592.

Wilson-Hench, J. W., and Hench, L. L. (1985). Tissue response to surface active materials. In: McKinney, R. (Ed.) Dental Implants, Chapter 10.

What is claimed is:

1. A composition comprising: (a) a bioactive ceramic; (b) anhydrous particles comprising at least one component of a biological fluid or of a synthetic biological fluid; and (c) a biocompatible resin.

2. The composition according to claim 1 wherein said anhydrous particles comprise $Na^+$ ions, $K^+$ ions, $Mg^{2+}$ ions, $Ca^{2+}$ ions, $Cl^-$ ions, $HCO_3^-$ ions, $SO_4^{2-}$ ions, or $HPO_4^{2-}$ or combinations thereof.

3. The composition according to claim 2 wherein said ions are dispersed in tris-(hydroxymethyl) aminomethane.

4. The composition according to claim 1 wherein said biocompatible resin is bisphenol-alpha-glycidyl methacrylate.

5. The composition according to claim 1 wherein said bioactive ceramic is a bioactive glass comprising Si, Ca, Na, $O_2$, H and P.

6. The composition according to claim 5 wherein said bioactive glass is 45S5 bioactive glass.

7. The composition of claim 2 wherein said composition comprises an intimate mixture of (a) said bioactive ceramic; (b) said anhydrous particles comprising the components of said biological fluid or said synthetic biological fluid; and (c) said biocompatible resin, whereby said composition is implanted into a recipient in need thereof without the need for measuring individual components at the time of implantation thereof.

8. The composition according to claim 1 comprising (a) 45S5 or other bioactive glass, (b) anhydrous particles comprising the components of biological or synthetic biological fluid comprising $Na^+$ ions, $K^+$ ions, $Mg^{2+}$ ions, $Ca^{2+}$ ions, $Cl^-$ ions, $HCO_3^-$ ions, $SO_4^{2-}$ ions, and $HPO_4^{2-}$ ions, and (c) bisphenol-alpha-glycidyl methacrylate.

9. The composition according to claim 7 wherein said biocompatible resin is a liquid.

10. The composition according to claim 7 wherein said composition is in the form of a paste or slurry.

11. The composition according to claim 7, said composition is comprised of discrete particles, wherein said discrete particles have an average size in the range between about 90 $\mu m$ and about 1000 $\mu m$.

12. The composition according to claim 11 wherein said discrete particles have an average size in the range between about 150 $\mu m$ and about 250 $\mu m$.

13. The composition according to claim 7, additionally comprising an implant having a surface, wherein said composition is applied to the surface of said implant.

14. The composition according to claim 1 further comprising growth factors, hormones, proteins, peptides, nucleic acids, and combinations thereof.

15. A method for inducing bone formation about an implant which comprises
contacting a bone implant site and an implant with a composition comprising (a) a bioactive ceramic; (b) anhydrous particles comprising at least one component of a biological fluid or of a synthetic biological fluid; and (c) a biocompatible resin.

16. The method according to claim 15 wherein said anhydrous particles comprising the components of biological fluid or synthetic biological fluid comprises $Na^+$ ions, $K^+$ ions, $Mg^{2+}$ ions, $Ca^{2+}$ ions, $Cl^-$ ions, $HCO_3$ ions, $SO_4^{2-}$ ions, or $HPO_4^{2-}$ ions, or combinations thereof.

17. The method according to claim 16 wherein said ions are dispersed in tris-(hydroxymethyl) aminomethane.

18. The method according to claim 15 wherein said biocompatible resin is bisphenolalpha-glycidyl methacrylate.

19. The method according to claim 15 wherein said bioactive ceramic is a bioactive glass comprising Si, Ca, Na, $O_2$, H and P.

20. The method according to claim 19 wherein said bioactive glass is 45S5 bioactive glass.

21. The method according to claim 15 wherein said composition comprises an intimate mixture of (a) said bioactive ceramic; (b) said anhydrous particles comprising the components of a biological fluid or of a synthetic biological fluid; and (c) said biocompatible resin, such that said composition may be implanted into a recipient in need thereof without the need for measuring individual components at the time of implantation thereof.

22. The method according to claim 15 comprising (a) 45S5 or other bioactive glass, (b) anhydrous particles comprising the components of biological or synthetic biological fluid comprising $Na^+$ ions, $K^+$ ions, $Mg^{2+}$ ions, $Ca^{2+}$ ions, $Cl^-$ ions, $HCO_3^-$ ions, $SO_4^{2-}$ ions, and $HPO_4^2$ ions, and (c) bisphenol-alpha-glycidyl methacrylate.

23. The method according to claim 21 wherein said biocompatible resin is a liquid.

24. The method according to claim 21 wherein said composition is in the form of a paste or slurry.

25. The method according to claim 21 wherein said composition is comprised of discrete particles, wherein said discrete particles have an average size in the range between about 90 $\mu$m and about 1000 $\mu$m.

26. The method according to claim 25 wherein said discrete particles have an average size in the range between about 150 $\mu$m and about 250 $\mu$m.

27. The method according to claim 21 wherein said composition is applied to the surface of an implant.

28. The method according to claim 15 wherein said composition further comprises growth factors, hormones, proteins, peptides, nucleic acids, and combinations thereof.

29. The composition of claim 1 wherein said anbydrous particles arc provided as pellets, which are dispersed in the composition.

30. The method of claim 15 wherein said anhydrous particles are provided as pellets, which are dispersed in the composition.

31. The composition according to claim 1, wherein said bioactive ceramic is a bioactive glass.

\* \* \* \* \*